(12) United States Patent
Ogata et al.

(10) Patent No.: US 9,012,690 B2
(45) Date of Patent: Apr. 21, 2015

(54) METHOD FOR PRODUCING ALCOHOL AND/OR AMINE FROM AMIDE COMPOUND

(75) Inventors: Osamu Ogata, Kanagawa (JP); Wataru Kuriyama, Kanagawa (JP); Takaji Matsumoto, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 85 days.

(21) Appl. No.: 13/825,449

(22) PCT Filed: Sep. 1, 2011

(86) PCT No.: PCT/JP2011/004897
§ 371 (c)(1),
(2), (4) Date: Mar. 21, 2013

(87) PCT Pub. No.: WO2012/039098
PCT Pub. Date: Mar. 29, 2012

(65) Prior Publication Data
US 2013/0172619 A1    Jul. 4, 2013

(30) Foreign Application Priority Data

Sep. 21, 2010  (JP) ................................ 2010-211338

(51) Int. Cl.
| | | |
|---|---|---|
| C07C 209/00 | (2006.01) | |
| C07C 209/50 | (2006.01) | |
| C07B 41/02 | (2006.01) | |
| C07B 43/04 | (2006.01) | |
| C07C 29/149 | (2006.01) | |
| C07C 209/62 | (2006.01) | |
| C07D 295/18 | (2006.01) | |
| C07C 29/36 | (2006.01) | |
| C07D 295/02 | (2006.01) | |

(52) U.S. Cl.
CPC ............... *C07C 209/50* (2013.01); *C07B 41/02* (2013.01); *C07B 43/04* (2013.01); *C07C 29/149* (2013.01); *C07C 209/62* (2013.01); *C07D 295/02* (2013.01); *C07D 295/18* (2013.01); *C07C 29/36* (2013.01)

(58) Field of Classification Search
CPC combination set(s) only.
See application file for complete search history.

(56) References Cited

U.S. PATENT DOCUMENTS

| 2005/0107638 A1 | 5/2005 | Abdur-Rashid |
| 2010/0010261 A1 | 1/2010 | Eastham et al. |

FOREIGN PATENT DOCUMENTS

| JP | 2010168357 A | 8/2010 |
| WO | 2008/035123 A2 | 3/2008 |

OTHER PUBLICATIONS

Mohri, et al., "Notification Concerning Transmittal of International Preliminary Report on Patentability (Chapter I of the Patent Cooperation Treaty)", Patent Cooperation Treaty, International Application No. PCT/JP2011/004897, mailed Apr. 4, 2013, The International Bureau of WIPO, Geneva, Switzerland, 6 pages.
John et al., "A Highly Active Catalyst for the Hydrogenation of Amides to Alcohols and Amines", Angewandte Chemie International Edition, vol. 50, No. 44, pp. 10377-10380 (2011).
Balaraman et al., "Direct Hydrogenation of Amides to Alcohols and Amines under Mild Conditions", Journal of the American Chemical Society, vol. 132, No. 47, pp. 16756-16758 (2010).
Käβ et al., "Ruthenium Complexes with Cooperative PNP Ligands: Bifunctional Catalysts for the Dehydrogenation of Ammonia-Borane", Angewandte Chemie International Edition, vol. 48, pp. 905-907 (2009).
Zhang et al., "Efficient Homogeneous Catalytic Hydrogenation of Esters to Alcohols", Angewandte Chemie International Edition, vol. 45, pp. 1113-1115 (2006).
Zhang et al., "Facile Conversion of Alcohols into Esters and Dihydrogen Catalyzed by New Ruthenium Complexes", Journal of the American Chemical Society, vol. 127, pp. 10840-10841 (2005).
Zhang et al., "Electron-Rich, Bulky Ruthenium PNP-Type Complexes. Acceptorless Catalytic Alcohol Dehydrogenation", Organometallics, vol. 23, pp. 4026-4033 (2004).
Nunez et al., "The synthesis of amines by the homogeneous hydrogenation of secondary and primary amides", Chem. Commun., pp. 3154-3156 (2007).

*Primary Examiner* — Clinton Brooks
(74) *Attorney, Agent, or Firm* — Mintz Levin Cohn Ferris Glovsky and Popeo, P.C.; Peter F. Corless

(57) ABSTRACT

Disclosed herein is a method for producing an alcohol and an amine from an amide under an atmosphere of hydrogen with the use of, as a catalyst, a ruthenium complex that is easily prepared, easy to handle, and relatively cheaply obtained. Specifically, the method is a method for producing an alcohol and/or an amine from an amide compound under an atmosphere of hydrogen with the use of as a catalyst, a ruthenium carbonyl complex represented by the following general formula (1): RuXY(CO)(L) (1) wherein X and Y may be the same or different from each other and each represents an anionic ligand and L represents a tridentate aminodiphosphine ligand containing two phosphino groups and a —NH— group.

19 Claims, No Drawings

METHOD FOR PRODUCING ALCOHOL AND/OR AMINE FROM AMIDE COMPOUND

CROSS-REFERENCES TO RELATED APPLICATIONS

This application is a 35 U.S.C. §371 U.S. national entry of International Application PCT/JP2011/004897 (WO 2012/039098) having an International filing date of Sep. 1, 2011, which claims under 35 U.S.C. §119(a) the benefit of Japanese Application No. 2010-211338, filed Sep. 21, 2010, the entire contents of which are incorporated herein by reference.

TECHNICAL FIELD

The present invention relates to a method for producing an alcohol and/or an amine from an amide compound under an atmosphere of hydrogen with the use of, as a catalyst, a ruthenium carbonyl complex having a tridentate ligand containing two phosphino groups and a —NH— group.

BACKGROUND ART

Alcohols and amines are useful compounds widely used in industrial applications, and therefore their production methods are important in industrial fields. An example of known methods for producing an alcohol or an amine is described in Reference Document 1 (Reductions by the Alumino-and Borohydrides in Organic Synthesis VCH Publishers, INC. 1991), in which an amide compound is reduced using a metal hydride. However, this method has problems such as the use of a dangerous metal hydride reagent and the generation of waste from the reagent theoretically required in an amount equal to or higher than that of the amide compound. For suchlike reason, there is a demand for a chemical synthesis technique that is more environmentally friendly and safer. An example of such a chemical synthesis method is the one in which alcohols or amines are catalytically produced from an amide compound under an atmosphere of hydrogen.

An example of a catalyst that catalyzes such a reaction is ruthenium complex. Along with platinum, rhodium, and iridium, the ruthenium complex is one of metals often used as a catalyst. However, the ruthenium complex is industrially advantageous in that it is cheaper than the other metals. An example of such a ruthenium complex is the one having a multidentate ligand. Patent Literature 1 discloses a dichloro complex as a ruthenium complex having a tridentate ligand containing two phosphino groups and a —NH— group, and Non-Patent Literature 1 discloses a dichloro complex or a hydride complex having trimethylphosphine as a ligand. However, these complexes have no carbonyl ligand. Further, Patent Literature 1 describes that the ruthenium dichloro complex catalyzes the hydrogenation reduction of ketones in the presence of a base so that an alcohol is obtained, but does not describe a method for obtaining an alcohol or an amine from an amide under an atmosphere of hydrogen. Non-Patent Literature 1 describes that the ruthenium phosphine complex acts as a catalyst for dehydrogenation of ammonia-borane, but does not describe a method for obtaining an alcohol or an amine from an amide under an atmosphere of hydrogen. Non-Patent Literatures 2, 3, and 4 disclose a ruthenium complex having a tridentate ligand containing two phosphino groups and a pyridine ring, and a carbonyl ligand, but this tridentate ligand does not contain a —NH— group. Further, it has been reported that the ruthenium phosphine complex used as a catalyst is unstable. Non-Patent Literatures 2 and 3 describe that alcohols can be synthesized by hydrogenation reduction of an ester with the pyridine ring-containing ruthenium complex as a catalyst, but do not describe a method for obtaining alcohols or amines from an amide under an atmosphere of hydrogen.

As methods for catalytically producing alcohols or amines from an amide under an atmosphere of hydrogen, methods described in Patent Literatures 2 and 3 and Non-Patent Literature 5 are known. However, the method described in Patent Literature 2 and the method described in Non-Patent Literature 5 are methods for obtaining an amine, and the structures of the amine obtained by these methods are different from the present invention. Even when an alcohol is produced, the alcohol is only obtained as a by-product or in a low yield. Patent Literature 3 discloses a cyclopentadienyl complex as a catalyst, but the cyclopentadienyl complex is different in structure from a catalyst used in the present invention. Further, the reaction time of about 24 to 90 hours and 1 to 10 mol % of a catalyst with respect to a substrate are required to achieve a sufficient conversion rate, except for cases where some substrates that achieve an exceptionally-high reaction rate are used.

CITATION LIST

Patent Literature

PTL 1: US Patent Application Publication No. 2005/0107638
PTL 2: US Patent Application Publication No. 20100010261
PTL 3: Japanese Patent Application Publication No. 2010-168357

Non Patent Literature

NPL 1: Angew. Chem. Int. Ed. 2009, 48, p. 905-907
NPL 2: Angew. Chem. Int. Ed. 2006, 45, p. 1113-1115
NPL 3: J. Am. Chem. Soc. 2005, 127, p. 10840-10841
NPL 4: Organometallics. 2004, 23, p. 4026-4033
NPL 5: Chem. Commun. 2007, 3154-3156

SUMMARY OF INVENTION

Technical Problem

An object of the present invention is to provide a technique for producing an alcohol and an amine from an amide compound under an atmosphere of hydrogen with a ruthenium complex that is easily prepared, easy to handle, and relatively cheaply obtained, as a catalyst.

Solution to Problem

In view of the above circumstances, the present inventors have extensively studied, and as a result, have found that alcohols or amines can be efficiently produced from an amide under relatively mild conditions and an atmosphere of hydrogen with the use of, as a catalyst, a ruthenium complex having a tridentate ligand containing two phosphino groups and a —NH— group and a carbonyl ligand. This finding has led to the completion of the present invention.

The method according to the present invention can be used also to remove an acyl group, which is a cheap and useful protective group for amines, for deprotection. As described in, for example, Reference Document 2 (Protective Groups in Organic Synthesis Second Edition, JOHN WILEY & SONS, INC. 1991), removal of an acyl group for deprotection requires heating under acidic conditions. However, the method according to the present invention makes it possible to perform deprotection relatively easily without exposure to acidic conditions. Further, the method according to the present invention is advantageous in that a basic amine generated as a result of deprotection can be purified without performing neutralization of a salt and subsequent extraction.

More specifically, the present invention relates to the following (1) to (10).

(1) A method for producing an alcohol and/or an amine from an amide compound represented by the following general formula (A) under an atmosphere of hydrogen in the presence of a ruthenium carbonyl complex represented by the following general formula (1):

[Chem. 1]

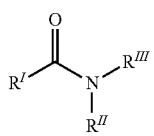
(A)

wherein R$^I$ represents hydrogen, an alkyl group, a cycloalkyl group, an aryl group, an aralkyl group, a heterocyclic group, an alkenyl group, an alkynyl group, or a cycloalkenyl group, these alkyl group, cycloalkyl group, aryl group, aralkyl group, heterocyclic group, alkenyl group, alkynyl group, and cycloalkenyl group may have one or more than one substituent, R$^{II}$ and R$^{III}$ may be the same or different from each other and each represents a hydrogen atom, an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkeny-loxycarbonyl group, an alkynyloxycarbonyl group, a cycloalkynyloxycarbonyl group, or a sulfonyl group, these alkyl group, cycloalkyl group, aryl group, aralkyl group, heterocyclic group, alkenyl group, alkynyl group, cycloalkenyl group, alkyloxy group, cycloalkyloxy group, aryloxy group, aralkyloxy group, hydroxyl group, alkoxycarbonyl group, cycloalkyloxycarbonyl group, aryloxycarbonyl group, aralkyloxycarbonyl group, alkenyloxycarbonyl group, alkynyloxycarbonyl group, cycloalkynyloxycarbonyl group, and sulfonyl group may have one or more than one substituent, and R$^I$ and R$^{II}$ and/or R$^{III}$ and R$^{II}$ may be linked together to form a ring; and RuXY(CO)(L)  (1)

wherein X and Y may be the same or different from each other and each represents an anionic ligand and L represents a tridentate aminodiphosphine ligand represented by the following general formula (2):

[Chem. 2]

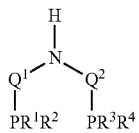
(2)

wherein R$^1$, R$^2$, R$^3$, and R$^4$ may be the same or different from one another and each represents a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group, R$^1$ and R$^2$ or R$^3$ and R$^4$ may be linked together to form a ring with an adjacent phosphorus atom, these alkyl group, cycloalkyl group, aryl group, aralkyl group, alkyloxy group, cycloalkyloxy group, aryloxy group, aralkyloxy group, heterocyclic group, and substituted amino group may have one or more than one substituent, Q$^1$ and Q$^2$ may be the same or different from each other and each represents a divalent alkylene group that may have one or more than one substituent, a divalent cycloalkylene group that may have one or more than one substituent, or a divalent aralkylene group that may have one or more than one substituent.

(2) The production method according to the above (1), wherein the tridentate aminodiphosphine ligand L is represented by the following general formula (3):

[Chem. 3]

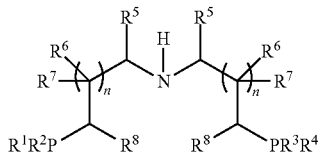
(3)

wherein R$^5$, R$^6$, R$^7$, and R$^8$ may be the same or different from one another and each represents a hydrogen atom, an alkyl group that may have one or more than one substituent, a cycloalkyl group that may have one or more than one substituent, an aryl group that may have one or more than one substituent, or an aralkyl group that may have one or more than one substituent, and n is an integer of 0 to 3.

(3) The production method according to the above (1) or (2), wherein the tridentate aminodiphosphine ligand L is represented by the following general formula (4):

[Chem. 4]

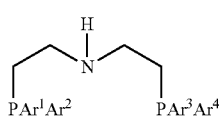
(4)

wherein Ar$^1$, Ar$^2$, Ar$^3$, and Ar$^4$ may be the same or different from one another and each represents an aryl group or an aromatic heterocyclic group, and these aryl group and aromatic heterocyclic group may have one or more than one substituent.

(4) The production method according to the above (3), wherein Ar$^1$, Ar$^2$, Ar$^3$, and Ar$^4$ in the general formula (4) are each a phenyl group that may have one or more than one substituent.

(5) The production method according to the above (4), wherein the tridentate aminodiphosphine ligand L is represented by the following general formula (5):

[Chem. 5]

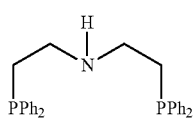
(5)

wherein Ph represents a phenyl group.

(6) The production method according to the above (1) or (2), wherein the tridentate aminodiphosphine ligand L is an optically active tridentate aminodiphosphine ligand.

(7) The production method according to any one of the above (1) to (6), wherein the anionic ligand represented by X in the general formula (1) is a hydride and the anionic ligand represented by Y in the general formula (1) is Cl.

(8) The production method according to any one of the above (1) to (6), wherein the anionic ligand represented by X in the general formula (1) is a hydride and the anionic ligand represented by Y in the general formula (1) is $BH_4$.

(9) The production method according to any one of the above (1) to (8), which is performed in the presence of a base.

(10) The production method according to the above (9), wherein the base is sodium methoxide.

Advantageous Effects of Invention

The ruthenium carbonyl complex of the present invention can be easily prepared from a tridentate aminodiphosphine ligand and a ruthenium carbonyl complex as a precursor. The tridentate aminodiphosphine ligand can be easily prepared by reacting a bisalkylamine having elimination groups with a phosphine compound in the presence of a base. Further, the ruthenium carbonyl complex as a precursor can be easily prepared from an easily available inorganic ruthenium compound. Such a ruthenium carbonyl complex of the present invention is not only easily prepared but also highly stable and easy to handle, and is therefore suitable for use in industrial applications. The ruthenium carbonyl complex of the present invention has high catalytic activity even under relatively mild reaction conditions, which makes it possible to efficiently produce an alcohol or an amine from an amide under an atmosphere of hydrogen and relatively mild conditions.

DESCRIPTION OF EMBODIMENTS

First, a ruthenium carbonyl complex of the present invention will be described. The ruthenium carbonyl complex is represented by the following formula (1):

RuXY(CO)(L)    (1)

wherein X and Y may be the same or different each other and each represents an anionic ligand and L represents a tridentate aminodiphosphine ligand represented by the following general formula (2):

[Chem. 6]

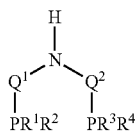    (2)

wherein $R^1$, $R^2$, $R^3$, and $R^4$ may be the same or different from one another and each represents a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group; $R^1$ and $R^2$ or $R^3$ and $R^4$ may be linked together to form a ring with an adjacent phosphorus atom; these alkyl group, cycloalkyl group, aryl group, aralkyl group, alkyloxy group, cycloalkyloxy group, aryloxy group, aralkyloxy group, and heterocyclic group may have one or more than one substituent; and $Q^1$ and $Q^2$ may be the same or different from each other and each represents a divalent alkylene group that may have one or more than one substituent, a divalent cycloalkylene group that may have one or more than one substituent, or a divalent aralkylene group that may have one or more than one substituent.

The tridentate aminodiphosphine ligand used in the present invention will be described. An example of the tridentate aminodiphosphine ligand represented by L in the general formula (1) has containing two phosphino groups and a —NH— group. A specific example of the tridentate aminodiphosphine ligand is the one represented by the above general formula (2).

$R^1$, $R^2$, $R^3$, and $R^4$ in the general formula (2) will be described.

An example of the alkyl group is a linear or branched alkyl group having 1 to 50 carbon atoms, preferably 1 to 20 carbon atoms, more preferably 1 to 10 carbon atoms. Specific examples thereof include a methyl group, an ethyl group, an n-propyl group, an isopropyl group, an n-butyl group, an isobutyl group, an s-butyl group, a tert-butyl group, an n-pentyl group, an n-hexyl group, an n-octyl group, and the like.

An example of the cycloalkyl group is a monocyclic, polycyclic, or fused-ring cycloalkyl group having 3 to 30 carbon atoms, preferably 3 to 20 carbon atoms, more preferably 3 to 10 carbon atoms. Specific examples thereof include a cyclopropyl group, a cyclopentyl group, a cyclohexyl group, and the like.

An example of the aryl group is a monocyclic, polycyclic, or fused-ring aryl group having 6 to 36 carbon atoms, preferably 6 to 18 carbon atoms, more preferably 6 to 14 carbon atoms. Specific examples thereof include a phenyl group, a naphthyl group, an anthryl group, a phenanthryl group, a biphenyl group, and the like.

An example of the aralkyl group is a group obtained by substituting at least one hydrogen atom of the above-mentioned alkyl group with the above-mentioned aryl group. For example, the aralkyl group preferably has 7 to 15 carbon atoms. Specific examples thereof include a benzyl group, a 1-phenylethyl group, a 2-phenylethyl group, a 1-phenylpropyl group, a 3-naphthylpropyl group, and the like.

An example of the alkyloxy group is an alkyloxy group having a liner or branched alkyl group having 1 to 20 carbon atoms, preferably 1 to 15 carbon atoms, more preferably 1 to 10 carbon atoms. Specific examples thereof include a methoxy group, an ethoxy group, an n-propoxy group, an isopropoxy group, an n-butoxy group, an isobutoxy group, an s-butoxy group, a tert-butoxy group, an n-pentyloxy group, and the like.

An example of the cycloalkyloxy group is a cycloalkyloxy group having a polycyclic or fused-ring cycloalkyl group having 3 to 20 carbon atoms, preferably 3 to 15 carbon atoms, more preferably 3 to 10 carbon atoms. Specific examples thereof include a cyclopropyloxy group, a cyclopentyloxy group, a cyclohexyloxy group, and the like.

An example of the aryloxy group is an aryloxy group having a monocyclic, polycyclic, or fused-ring aryl group having 6 to 36 carbon atoms, preferably 6 to 18 carbon atoms, more preferably 6 to 14 carbon atoms. Specific examples thereof include a phenoxy group, a tolyloxy group, a xylyloxy group, a naphtoxy group, and the like.

An example of the aralkyloxy group is a group obtained by substituting at least one hydrogen atom of the alkyl group of the above-mentioned alkyloxy group or of the above-mentioned cycloalkyl group with the above-mentioned aryl group. For example, the aralkyloxy group preferably has 7 to 15 carbon atoms. Specific examples thereof include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphthylmethoxy group, a 2-naphthylmethoxy group, and the like.

Examples of the heterocyclic group include an aliphatic heterocyclic group and an aromatic heterocyclic group. An example of the aliphatic heterocyclic group is a 3- to 8-membered (preferably 4- to 6-membered) monocyclic, polycyclic, or fused-ring aliphatic heterocyclic group having 2 to 14 carbon atoms and at least one heteroatom (preferably 1 to 3 heteroatoms) such as a nitrogen atom, an oxygen atom, and/or a sulfur atom. Specific examples of such an aliphatic heterocyclic group include an azetidyl group, an azetidino group, a pyrrolidyl group, a pyrrolidino group, a piperidinyl group, a piperidino group, a piperadinyl group, a piperadino group, a morpholinyl group, a morpholino group, a tetrahydrofuryl group, a tetrahydropyranyl group, a tetrahydrothiophenyl group, and the like.

An example of the aromatic heterocyclic group is a 5- or 6-membered monocyclic, polycyclic, or fused-ring heteroaryl group having 4 to 15 carbon atoms and at last one heteroatom (preferably 1 to 3 heteroatoms) such as a nitrogen atom, an oxygen atom, and/or a sulfur atom. Specific examples thereof include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a cinnolyl group, a benzoimidazolyl group, a benzoxazolyl group, a benzothiazolyl group, an acridyl group, an acridinyl group, and the like.

An example of the substituted amino group is an amino group obtained by substituting two hydrogen atoms of an amino group with the above-mentioned alkyl, cycloalkyl, aryl, aralkyl, and/or heterocyclic groups which are the same or different from each other. Specific examples thereof include: a dialkylamino group such as an N,N-diethylamino group or an N,N-diisopropylamino group; a dicycloalkylamino group such as an N,N-dicyclohexylamino group; a diarylamino group such as an N,N-diphenylamino group or an N-naphthyl-N-phenylamino group; a diaralkylamino group such as an N,N-dibenzylamino group, and the like. The alkyl group, the cycloalkyl group, the aryl group, the aralkyl group, and the heterocyclic group as substituents of the substituted amino group may further have one or more than one sub-stituent.

Examples of the substituents that may be possessed by the alkyl group, the cycloalkyl group, the aryl group, the aralkyl group, the alkyloxy group, the cycloalkyloxy group, the aryloxy group, the aralkyloxy group, the heterocyclic group, and the alkyl group, the cycloalkyl group, the aryl group, the aralkyl group, and the heterocyclic group on the substituted amino group include the above-mentioned alkyl group, cycloalkyl group, aryl group, aralkyl group, alkyloxy group, cycloalkyloxy group, aryloxy group, aralkyloxy group, heterocyclic group, substituted amino group, a halogen atom, a silyl group, an optionally-protected hydroxyl group, and the like.

Examples of the halogen atom as substituents of $R^1$, $R^2$, $R^3$, and $R^4$ include a fluorine atom, a chlorine atom, a bromine atom, and an iodine atom.

Examples of the silyl group as substituents of $R^1$, $R^2$, $R^3$, and $R^4$ include one obtained by replacing three hydrogen atoms of a silyl group with the above-mentioned alkyl, cycloalkyl, aryl, and/or aralkyl groups, and the like. Specific examples thereof include a trimethylsilyl group, a triethylsilyl group, a t-butyldimethylsilyl group, a tbutyldiphenylsilyl group, a triphenylsilyl group, and the like.

Examples of the optionally-protected hydroxyl group as substituents of $R^1$, $R^2$, $R^3$, and $R^4$ include a unprotected hydroxyl group and hydroxyl groups that may be protected by common protective groups for a hydroxyl group for use in, for example, peptide synthesis which are described in, for example, Reference Document 2 (Protective Groups in Organic Synthesis Second Edition, JOHN WILEY & SONS, INC. 1991). Examples of such protective groups include a silyl group such as a trimethylsilyl group, a tert-butyldimethylsilyl group, and a tert-butyldiphenylsilyl group, a benzyl group, a methoxymethyl group, and the like.

$Q^1$ and $Q^2$ in the general formula (2) will be described.

An example of the divalent alkylene group is a linear or branched divalent alkyl chain having 1 to 20 carbon atoms, preferably 1 to 10 carbon atoms, more preferably 1 to 6 carbon atoms. Specific examples thereof include a methylene group, an ethylene group, a trimethylene group, a tetramethylene group, a pentamethylene group, and the like.

An example of the divalent cycloalkylene group is a divalent group having a monocyclic, polycyclic, or fused-ring cycloalkyl group having 3 to 15 carbon atoms, preferably 3 to 10 carbon atoms, more preferably 3 to 6 carbon atoms. Specific examples thereof include a cyclopropylene group, a cyclobutylene group, a cyclopenthylene group, a cyclohexylene group, and the like.

An example of the divalent aralkylene group is a divalent group having 7 to 11 carbon atoms, which is obtained by removing one hydrogen atom from an aryl group of an aralkyl group such as a benzyl group or a phenethyl group. Specific examples thereof include a benzylene group (-Ph-CH$_2$—), a 2-phenylethylene group (-Ph-CH$_2$CH$_2$—), a 1-naphthylmethylene group (—Np—CH$_2$—), a 2-naphthylmethylene group (—Np—CH$_2$—), and the like (in these formulas, -Ph- represents a phenylene group and —Np— represents a naphthylene group).

Examples of the substituents that may be possessed by the divalent alkylene group, the divalent cycloalkylene group, or the divalent aralkylene group include the alkyl group, the cycloalkyl group, the aryl group, the aralkyl group, the alkyloxy group, the cycloalkyloxy group, the aryloxy group, the aralkyloxy group, the heterocyclic group, the halogen atom, the silyl group, the substituted amino group, the optionally-protected hydroxyl group, and the like, which have been described above with reference to $R^1$, $R^2$, $R^3$, and $R^4$ in the general formula (2).

Hereinbelow, a monovalent anionic ligand represented by X or Y in the general formula (1) will be described.

Examples of the monovlalent anionic ligand include a hydride, an alkyloxy group, a cycloalkyloxy group, an aryloxy group, an aralkyloxy group, a hydroxy group, an acyloxy group, a sulfonyloxy group, a halogen ion, AlH$_4$-, AlH$_2$(OCH$_2$CH$_2$OCH$_2$)$_2$-, BH$_4$-, BH$_3$CN-, BH(Et)$_3$-, BH(sec-Bu)$_3$-, and the like. Among them, BH$_4$, a hydride, and a chlorine ion are preferred. It is to be noted that, in this specification, a hydride is also sometimes simply referred to as "hydrogen" and a halogen ion is also sometimes simply referred to as "halogen".

An example of the acyloxy group is the one represented by ($R^aCO_2$). Examples of $R^a$ in the acyloxy group ($R^aCO_2$) include a hydrogen atom, an alkyl group, a cycloalkyl group, an aryl group, and an aralkyl group. Examples of the alkyl group, the cycloalkyl group, the aryl group, and the aralkyl group include those described above with reference to $R^1$, $R^2$, $R^3$, and $R^4$ in the general formula (2). These alkyl group, cycloalkyl group, aryl group, and aralkyl group may further have one or more than one substituent, and examples of such substituents include the alkyl group, the cycloalkyl group, the aryl group, the aralkyl group, the alkyloxy group, the cycloalkyloxy group, the aralkyloxy group, the aryloxy group, the heterocyclic group, the halogen atom, the silyl group, and the optionally-protected hydroxyl group which have been described above with reference to $R^1$, $R^2$, $R^3$, and $R^4$ in the general formula (2), an optionallyprotected amino group, and the like.

Examples of the optionally-protected amino group as substituents of $R^a$ include: an unprotected amino group; a mono- or dialkylamino group such as an N-methylamino group, an N,N-dimethylamino group, an N,N-diethylamino group, an N,N-diisopropylamino group, or an N-cyclohexylamino group; a mono- or diarylamino group such as an N-phenylamino group, an N,N-diphenylamino group, an N-naphthylamino group, or an N-naphthyl-N-phenylamino group; a mono- or diar-alkylamino group such as an N-benzylamino group or an N,N-dibenzylamino group; an acylamino group such as a formylamino group, an acetylamino group, a propionylamino group, a pivaloylamino group, a pentanoylamino group, a hexanoylamino group, or a benzoylamino group; an alkoxycarbonylamino group such as a methoxycarbonylamino group, an ethoxycarbonylamino group, an n-propoxycarbonylamino group, an n-butoxycarbonylamino group, a tert-butoxycarbonylamino group, a pentyloxycarbonylamino group, or a hexyloxycarbonylamino group; an aryloxycarbonylamino group such as a phenyloxycarbonylamino group; an aralkyloxycarbonylamino group such as a benzyloxycarbonylamino group, and the like. Other examples of the optionally-protected amino group include amino groups protected by common protective groups for amino groups for use in, for example, peptide synthesis, and the like which are described in, for example, the above-mentioned Reference Document 1.

Specific examples of $R^a$ include a methyl group, an ethyl group, a propyl group, a tert-butyl group, a trifluoromethyl group, a phenyl group, a pentafluorophenyl group, and the like.

An example of the sulfonyloxy group is the one represented by ($RsSO_3$). Examples of $R^5$ in the sulfonyloxy group $RsSO_3$ are the same as the above-mentioned examples of $R^a$ in the acyloxy group.

Examples of the halogen ion include a fluorine ion, a chlorine ion, a bromine ion, and an iodine ion. Among them, a chlorine ion and a bromine ion are preferred, and a chlorine ion is more preferred.

A preferred example of the tridentate aminophosphine ligand is the one represented by the following general formula (3).

[Chem. 7]

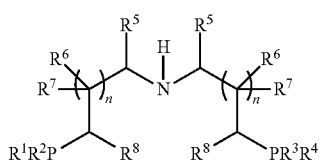

(3)

wherein $R^5$, $R^6$, $R^7$, and $R^8$ may be the same or different from one another and each represents a hydrogen atom, an alkyl group, a cycloalkyl group, an aryl group, or an aralkyl group; $R^5$ and $R^5$, $R^5$ and $R^6$, $R^7$, or $R^8$, or $R^6$ and $R^7$ or $R^8$ may be linked together to form a ring together with an adjacent carbon atom(s); n is an integer of 0 to 3; and these alkyl group, cycloalkyl group, aryl group, and aralkyl group may have one or more than one substituent.

Examples of the alkyl group, the cycloalkyl group, the aryl group, and the aralkyl group represented by $R^5$, $R^6$, $R^7$, and $R^8$ in the general formula (3) include those described above with reference to $R^1$, $R^2$, $R^3$, and $R^4$ in the general formula (2). Examples of the substituents that may be possessed by these alkyl group, cycloalkyl group, aryl group, and aralkyl group include the alkyl group, the cycloalkyl group, the aryl group, the aralkyl group, the alkyloxy group, the cycloalkyloxy group, the aryloxy group, the aralkyloxy group, the heterocyclic group, the halogen atom, the silyl group, the substituted amino group, the optionally-protected hydroxyl group, and the like, which have been described above with reference to $R^1$, $R^2$, $R^3$, and $R^4$ in the general formula (2).

A more preferred example of the tridentate aminodiphosphine ligand is the one represented by the following general formula (4).

[Chem. 8]

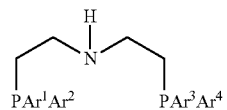

(4)

wherein $Ar^1$, $Ar^2$, $Ar^3$, and $Ar^4$ may be the same or different from one another and each represents an aryl group or an aromatic heterocyclic group, and these aryl group and aromatic heterocyclic group may have one or more than one substituent.

Examples of the aryl group and the aromatic heterocyclic group in the general formula (4) include the aryl group, the aromatic heterocyclic group as an example of the heterocyclic group, and the like, which have been described above with reference to $R^1$, $R^2$, $R^3$, and $R^4$ in the general formula (2). Examples of the substituents that may be possessed by these aryl group and aromatic heterocyclic group include the alkyl group, the cycloaklyl group, the aryl group, the aralkyl group, the alkyloxy group, the cycloalkyloxy group, the aryloxy group, the aralkyloxy group, the halogen atom, the silyl group, the heterocyclic group, the substituted amino group, the optionally-protected hydroxyl group, and the like, which have been described above with reference to $R^1$, $R^2$, $R^3$, and $R^4$ in the general formula (2).

An even more preferred example of the tridentate aminodiphosphine ligand is the one represented by the following general formula (5).

[Chem. 9]

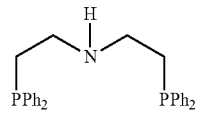

(5)

The tridentate aminodiphosphine ligand represented by the general formula (2) or (3) may be used as an optically active ligand of the ruthenium carbonyl complex represented by the general formula (1) depending on the substituents on $Q^1$ and $Q^2$ or $R^1$ to $R^8$.

A ruthenium compound as a starting material for producing a ruthenium carbonyl complex used in the present invention is not particularly limited, and examples thereof include inorganic ruthenium compounds such as a $RuCl_3$ hydrate, a $RuBr_3$ hydrate, and a $RuI_3$ hydrate, $RuCl_2(DMSO)_4$, [Ru(cod)$Cl_2]_n$, [Ru(nbd)$Cl_2]_n$, (cod)Ru(2-methallyl)$_2$, [Ru(benzene)$Cl_2]_2$, [Ru(benzene)$Br_2]_2$, [Ru(benzene)$I_2]_2$, [Ru(p-cymene)$Cl_2]_2$, [Ru(p-cymene)$Br_2]_2$, [Ru(p-cymene)$I_2]_2$, [Ru(mesitylene)$Cl_2]_2$, [Ru(mesitylene)$Br_2]_2$, [Ru(mesitylene)$I_2]_2$, [Ru(hexamethylbenzene)$Cl_2]_2$, [Ru(hexamethylbenzene)$Br_2]_2$, [Ru(hexamethylbenzene)$I_2]_2$, $RuCl_2(PPh_3)_3$, $RuBr_2(PPh_3)_3$, $RuI_2(PPh_3)_3$, $RuH_4(PPh_3)_3$, $RuClH(PPh_3)_3$, $RuH(OAc)(PPh_3)_3$, $RuH_2(PPh_3)_4$, and the like. In the above examples, DMSO represents dimethylsulfoxide, cod represents 1,5-cyclooctadiene, nbd represents norbornadiene, and Ph represents a phenyl group.

The ruthenium carbonyl complex represented by the general formula (1) can be easily prepared from a tridentate aminodiphosphine ligand and a ruthenium carbonyl complex as a precursor.

The tridentate aminodiphosphine ligand can be easily prepared by reacting a bis(substituted alkyl)amine having an elimination groups with a phosphide compound of an alkali metal such as lithium, sodium, or potassium.

The ruthenium carbonyl complex as a precursor can be obtained by, for example, a method described in Inorg. Synth, 1974, 15, 45. The obtained ruthenium carbonyl complex as a precursor is reacted with the tridentate aminodiphosphine ligand to prepare a tridentate aminodiphosphine ligand-containing ruthenium carbonyl complex used in the present invention.

For example, the ruthenium carbonyl complex represented by the general formula (1) can be produced by reacting the tridentate aminodiphosphine ligand L represented by the general formula (2) with $RuXY(CO)(P(Ar^5)_3)_3$ (wherein $Ar^5$s may be the same or different from one another and each represents an aryl group that may have one or more than one substituent). Examples of the aryl group or the substituents thereof in $Ar^5$ include those mentioned above. Examples of the preferred $Ar^5$ are a phenyl group that may have one or more than one substituent, particularly a phenyl group.

The ruthenium carbonyl complex represented by the general formula (1) wherein X is $BH_4$ can be produced by reacting the ruthenium carbonyl complex wherein X is a chlorine ion with $NaBH_4$ according to, for example, a method described in J. Am. Chem. Soc. 2005, 127, 516.

The complex prepared in such a manner as described above may have stereoisomers due to the coordination or conformation of the ligands. The complex used in the reaction may be a mixture of these stereoisomers or a pure single isomer. These complexes present relatively stably and are easy to handle.

A preferred example of the complex is the one represented by the following general formula (8):

wherein (L) represents a tridentate aminodiphosphine represented by the above general formula (5). This complex is easily prepared by appropriately mixing the tridentate aminodiphosphine ligand L represented by the general formula (5) and $RuClH(CO)(PPh_3)_3$ in a solvent.

Another preferred example of the complex is the one represented by the following general formula (9):

wherein L represents a tridentate aminodiphoshine represented by the above general formula (5). The complex is easily prepared by appropriately mixing the ruthenium carbonyl complex represented by the general formula (8) and $NaBH_4$ in a solvent.

The use of such a ruthenium carbonyl complex as a catalyst makes it possible to produce, from an amide, a corresponding alcohol or amine under an atmosphere of hydrogen in a good yield with high catalyst efficiency.

Hereinbelow, an amide compound, an alcohol, and an amine in the present invention will be described. An amide compound used as a substrate of a raw material in the present invention may be substituted with any substituent that does not have adverse effects on a catalytic synthesis method according to the present invention. A method for producing an alcohol and/or an amine from an amide compound according to the present invention is a method for producing, from an amide compound, a corresponding alcohol (B) and/or a corresponding amine (C) by performing a reaction represented by the following chemical equation (D) under an atmosphere of hydrogen with the use of a ruthenium carbonyl complex represented by the general formula (1):

[Chem. 10]

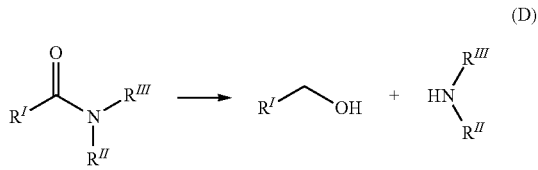

wherein $R^I$ represents hydrogen, an alkyl group, a cycloalkyl group, an aryl group, an aralkyl group, a heterocyclic group, an alkenyl group, an alkynyl group, or a cycloalkenyl group; these alkyl group, cycloalkyl group, aryl group, aralkyl group, heterocyclic group, alkenyl group, alkynyl group, and cycloalkenyl group may have one or more than one substituent; $R^{II}$ and $R^{III}$ may be the same or different from each other and each represents a hydrogen atom, an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, a cycloalkynyloxycarbonyl group, or a sulfonyl group; these alkyl group, cycloalkyl group, aryl group, aralkyl group, heterocyclic group, alkenyl group, alkynyl group, cycloalkenyl group, alkyloxy group, cycloalkyloxy group, aryloxy group, aralkyloxy group, hydroxyl group, alkoxycarbonl group, cycloalkyloxycarbonyl group, aryloxycarbonyl group, aralkyloxycarbonyl group, alkenyloxycarbonyl group, alkynyloxycarbonyl group, cycloalkynyloxycarbonyl group, and sulfonyl group may have one or more than one substituent; and $R^I$ and $R^{II}$ and/or $R^{III}$, and $R^{II}$ and $R^{III}$ may be linked together to form a ring.

The generated alcohol (B) is represented by the following general formula (B):

wherein $R^I$ is the same as that described above.

The generated amine (C) is represented by the following general formula (C):

wherein $R^{II}$ and $R^{III}$ are the same as those described above.

The method according to the present invention is a method for producing, from an amide compound, a corresponding alcohol (B) and a corresponding amine (C) at the same time. However, when attention is focused on only one of the products (i.e., on only one of the alcohol (B) and the amine (C)), the method according to the present invention can be regarded as a method for producing only one of the compounds (i.e., only one of the alcohol (B) and the amine (C)).

As will be described below, when the amide compound forms a ring, that is, when the amide compound is a lactam, $R^I$ of the alcohol (B) and $R^{II}$ and/or $R^{III}$ of the amine (C) are linked together so that an amino alcohol is obtained as a product.

$R^I$, $R^{II}$, and $R^{III}$ in the general formula (A) will be described. Examples of the alkyl group, the cycloalkyl group, the aryl group, the aralkyl group, and the heterocyclic group represented by $R^I$ include those described above with reference to $R^1$, $R^2$, $R^3$, and $R^4$ in the general formula (2). An example of the alkenyl group represented by $R^I$ is a linear or branched alkenyl group having 2 to 20 carbon atoms, preferably 2 to 15 carbon atoms, more preferably 2 to 10 carbon atoms. Specific examples thereof include an ethenyl group, a propenyl group, a 1-butenyl group, a pentenyl group, a hexenyl group, a heptenyl group, an octenyl group, a nonenyl group, a decenyl group, and the like. An example of the alkynyl group represented by $R^I$ is a linear or branched alkynyl group having 2 to 20 carbon atoms, preferably 2 to 15 carbon atoms, more preferably 2 to 10 carbon atoms. Specific examples thereof include an ethynyl group, a 1-propynyl group, a 2-propynyl group, a 1-butynyl group, a 3-butynyl group, a pentynyl group, a hexynyl group, and the like. An example of the cycloalkenyl group represented by $R^I$ is a 4- to 10-membered mono- to tricyclic aliphatic hydrocarbon group having one or two double bonds in the ring. Specific examples thereof include a cyclobutenyl group, a cyclopentenyl group, a cyclohexenyl group, a cycloheptenyl group, and a cyclooctenyl group.

Examples of the substituents that may be possessed by these alkyl group, cycloalkyl group, aryl group, aralkyl group, the heterocyclic group, alkenyl group, alkynyl group, and cycloalkenyl group include the alkyl group, the cycloalkyl group, the aryl group, the aralkyl group, the alkyloxy group, the cycloalkyloxy group, the aryloxy group, the aralkyloxy group, the halogen atom, the silyl group, the heterocyclic group, the optionally-protected amino group, the optionally-protected hydroxyl group, and the like, which have been described above with reference to $R^1$, $R^2$, $R^3$, and $R^4$ in the general formula (2) and the alkenyl group, the alkynyl group, the cycloalkenyl group, the alkoxycarbonyl group, the cycloalkyloxycarbonyl group, the aryloxycarbonyl group, the aralkyloxycarbonyl group, the alkenyloxy group, the alkynyloxy group, and the cycloalkynyloxy group which have been described above with reference to $R^I$ in the general formula (A). It is to be noted that when the protective group for the optionally-protected hydroxyl or amino group is an acyl group, there is a case where a resulting product does not have the protective group. Further, when the alkoxycarbonyl group, the cycloalkyloxycarbonyl group, the aryloxycarbonyl group, the aralkyloxycarbonyl group, the alkenyloxycarbonyl group, the alkynyloxycarbonyl group, or the cycloalkynyloxycarbonyl group is present as the substituents, there is a case where a product reduced by hydrogenation is formed.

Examples of the alkoxycarbonyl group, the cycloalkyloxycarbonyl group, the aryloxycarbonyl group, the aralkyloxycarbonyl group, the alkenyloxycarbonyl group, the alkynyloxycarbonyl group, and the cycloalkynyloxycarbonyl group as the substituents include those represented by the following general formula (13):

[Chem. 11]

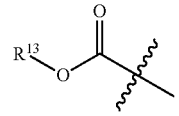

(13)

Wherein $R^{II}$ represents an alkyl group, a cycloalkyl group, an aryl group, an aralkyl group, a heterocyclic group, an alkenyl group, an alkynyl group, or a cycloalkenyl group, and these alkyl group, cycloalkyl group, aryl group, aralkyl group, heterocyclic group, alkenyl group, alkynyl group, and cycloalkenyl group may have one or more than one substituent.

$R^{13}$ in the general formula (13) will be described. Examples of the alkyl group, the cycloalkyl group, the aryl group, the aralkyl group, and the heterocyclic group include those described above with reference to $R^1$, $R^2$, $R^3$, and $R^4$ in the general formula (2). Examples of the alkenyl group, the alkynyl group, and the cycloalkenyl group include those described above with reference to $R^I$ and $R^{II}$ in the general formula (A).

Examples of the substituents that may be possessed by $R^{13}$ in the general formula (13) include the alkyl group, the cycloalkyl group, the aryl group, the aralkyl group, the heterocyclic group which have been described above with reference to $R^1$, $R^2$, $R^3$, and $R^4$ in the general formula (2) and the alkenyl group, the alkynyl group, and the cycloalkenyl group which have been described above with reference to $R^I$ in the general formula (A).

Examples of the alkyl group, the cycloalkyl group, the aryl group, the aralkyl group, the heterocyclic group, the alkenyl group, the alkynyl group, and the cycloalkenyl group represented by $R^{II}$ and $R^{III}$ include those described above with reference to $R^I$. Examples of the alkyloxy group, the cycloalkyloxy group, the aryloxy group, and the aralkyloxy group represented by $R^{II}$ and $R^{III}$ include those described above with reference to $R^1$, $R^2$, $R^3$, and $R^4$ in the general formula (2). Examples of the substituents that may be possessed by these alkyl group, cycloalkyl group, aryl group, aralkyl group, heterocyclic group, alkenyl group, alkynyl group, cycloalkenyl group, alkyloxy group, cycloalkyloxy group, aryloxy group, and aralkyloxy group include the alkyl group, the cycloalkyl group, the aryl group, the aralkyl group, the alkyloxy group, the cycloalkyloxy group, the aryloxy group, the aralkyloxy group, the halogen atom, the silyl group, the heterocyclic group, the optionally-protected amino group, the optionally-protected hydroxyl group, and the like, which have been described above with reference to $R^1$, $R^2$, $R^3$, and $R^4$ in the general formula (2) and the alkenyl group, the alkynyl group, the cycloalkenyl group, the alkoxycarbonyl group, the cycloalkyloxycarbonyl group, the aryloxycarbonyl group, the aralkyloxycarbonyl group, the alkenyloxy group, the alkynyloxy group, and the cycloalkynyloxy group which have been described above with reference to $R^I$ in the general formula (A). It is to be noted that when the protective group for the optionally-protected hydroxyl or amino group is an acyl group, there is a case where a resulting product does not have the protective group.

Examples of the alkoxycarbonyl group, the cycloalkyloxycarbonyl group, the aryloxycarbonyl group, the aralkyloxycarbonyl group, the alkenyloxycarbonyl group, the alkynyloxycarobnyl group, and the cycloalkynyloxycarbonyl group represented by $R^{II}$ and $R^{III}$ include those described above as the substituents that may be possessed by the alkyl group, the cycloalkyl group, the aryl group, the aralkyl group, the heterocyclic group, the alkenyl group, the alkynyl group, and the cycloalkenyl group represented by $R^{I}$.

It is to be noted that when the alkoxycarbonyl group, the cycloalkyloxycarbonyl group, the aryloxycarbonyl group, the aralkyloxycarbonyl group, the alkenyloxycarbonyl group, the alkynyloxycarobnyl group, or the cycloalkynyloxycarbonyl group is present as the substituents, there is a case where a product reduced by hydrogenation is formed.

In the reaction according to the present invention, when $R^{I}$ and $R^{II}$ and/or $R^{III}$ form a ring, preferably when $R^{I}$ and $R^{II}$ or $R^{III}$ form a ring (i.e., when $R^{I}$ and $R^{II}$ form a ring or when $R^{I}$ and $R^{III}$ form a ring), the compound represented by the general formula (A) is a lactam. When a ring is formed by $R^{I}$ and $R^{II}$ and/or $R^{III}$, $R^{I}$ and $R^{II}$ and/or $R^{III}$ need to be linked together. When $R^{I}$ and $R^{II}$ and $R^{III}$ are linked together, $R^{I}$ releases two hydrogen atoms, and is chemically linked to a position on $R^{II}$ from which one hydrogen atom has been removed and to a position on $R^{III}$ from which one hydrogen atom has been removed so that a ring is formed. When $R^{I}$ and $R^{II}$ or $R^{III}$ are linked together, $R^{I}$ releases one hydrogen atom, and is chemically linked to a position on RII or $R^{III}$ from which one hydrogen atom has been removed so that a ring is formed.

As described above, when $R^{I}$ and $R^{II}$ and/or $R^{III}$ form a ring, the compound represented by the general formula (A) is a lactam. In this case, an amino alcohol is obtained as a reduction product, in which $R^{I}$ in the alcohol (B) and $R^{II}$ and/or $R^{III}$ in the amine (C) are linked together.

An example of the sulfonyl group represented by $R^{II}$ and $R^{III}$ is one represented by ($R^{SI}SO_2$). Examples of $R^{SI}$ in the sulfonyl group $R^{SI}SO_2$ are the same as the above-mentioned examples of $R^{S}$ in the sulfonyloxy group. Further, $R^{SI}$ may be linked to $R^{I}$, $R^{II}$, or $R^{III}$ to form a ring.

The method for producing an alcohol and/or an amine according to the present invention can be properly performed without any solvent or in a solvent, but is preferably performed in a solvent. The solvent to be used is preferably capable of dissolving the substrate and the catalyst, and may be a single solvent or a mixed solvent. Specific examples of such a solvent include: aromatic hydrocarbons such as toluene and xylene; aliphatic hydrocarbons such as hexane and heptane; halogenated hydrocarbons such as methylene chloride and chlorobenzene; ethers such as diethyl ether, tetrahydrofuran, methyl tert-butyl ether, and cyclopentyl methyl ether; alcohols such as methanol, ethanol, isopropyl alcohol, n-butyl alcohol, 2-butanol, and tert-butyl alcohol; and polyhydric alcohols such as ethylene glycol, propylene glycol, 1,2-propanediol, and glycerin. Among them, ethers and alcohols are preferred, and tetrahydrofuran, methanol, and isopropanol are particularly preferred. The amount of the solvent to be used can be appropriately selected depending on, for example, reaction conditions. If necessary, the reaction is performed with stirring.

The amount of the catalyst to be used depends on, for example, the type of catalyst used, the type of amide used as a substrate, reaction conditions, or the like, but a molar ratio of a ruthenium metal to the amide as a substrate is usually 0.0001 mol % to 10 mol %, preferably 0.005 mol % to 5 mol %. According to the method of the present invention, the reaction temperature during hydrogenation reduction is 0 to 180 degrees C., preferably 0 to 120 degrees C. If the reaction temperature is too low, there is a case where a large amount of the unreacted raw material remains. On the other hand, if the reaction temperature is too high, there is a case where decomposition of, for example, the raw material, the catalyst, and the like undesirably occurs.

According to the method of the present invention, the pressure of hydrogen during hydrogen reduction is 0.1 to 10 MPa, preferably 3 to 6 MPa. Further, the reaction time is 30 minutes to 72 hours, preferably 2 to 48 hours, which makes it possible to achieve a sufficiently high raw material conversion rate.

After the completion of the reaction, a target alcohol is obtained by using, singly or in combination, purification techniques usually used such as extraction, filtration, crystallization, distillation, and various chromatography techniques.

According to the present invention, the reaction may be performed by adding an appropriate additive.

An example of the additive is a basic compound. Specific examples of the basic compound include amines such as triethylamine, diisopropylethylamine, N,N-dimethylaniline, piperidine, pyridine, 4-dimethylaminopyridine, 1,5-diazabicyclo[4.3.0]nona-5-ene, 1,8-diazabicyclo[5.4.0]undeca-7-ene, trin-butylamine, and N-methylmorpholine; alkali metal carbonates such as potassium carbonate, sodium carbonate, lithium carbonate, and cesium carbonate; alkaline-earth metal carbonates such as magnesium carbonate and calcium carbonate; alkali metal hydrogen carbonates such as sodium hydrogen carbonate and potassium hydrogen carbonate; alkali metal hydroxides such as sodium hydroxide, potassium hydroxide, and lithium hydroxide; alkaline-earth metal hydroxides such as magnesium hydroxide and calcium hydroxide; alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium isopropoxide, and lithium tert-butoxide; alkaline-earth metal alkoxides such as magnesium methoxide and magnesium ethoxide; and metal hydrides such as sodium hydride and potassium hydride. Among these bases, sodium methoxide and potassium tert-butoxide are particularly preferred.

EXAMPLES

The present invention will be described in detail with reference to the following Examples, but the present invention is not limited to these Examples.

It is to be noted that the reaction was evaluated by determining an isolated yield or a gas chromatography (GC) area percentage (%). Apparatuses used are as follows.

GC system GC-2010 manufactured by Shimadzu Corporation

GC; capillary Neutra Bond-1

Injection temperature: 220 degrees C., Detection temperature: 250 degrees C. 40 degrees C. (0 min)-5 degrees C./min-100 degrees C.-10 degrees C./min-250 degrees C. (8 min)

$^1$H-NMR spectrum and $^{31}$P-NMR spectrum were measured using MERCURY plus 300 manufactured by Varian.

Example 1

A ruthenium carbonyl complex 1 was produced according to the following equation.

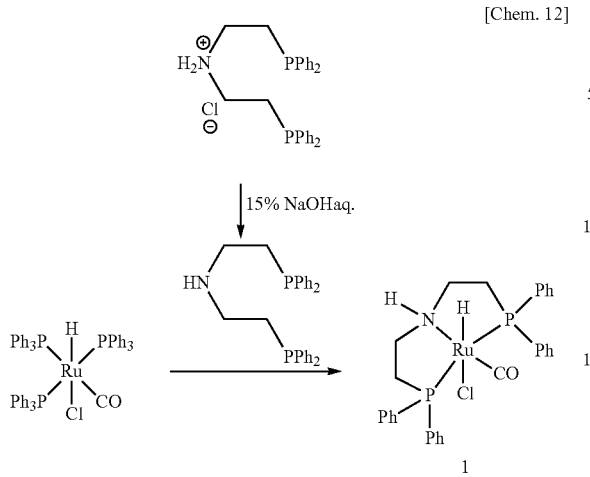

Under the stream of nitrogen, 4.18 mmol of amine hydrochloride shown in the above equation was placed in a 100 mL-flask and suspended in 33 mL of toluene, and 14 mL of 15% aqueous NaOH solution was added thereto and the resulting mixture was stirred at room temperature until no solid remained. The resulting solution was separated into an organic phase and an aqueous phase, and the organic phase was washed with 14 mL of distilled water (2 times) and the aqueous phase was subjected to extraction with 14 mL of toluene (2 times). The thus obtained organic phases were mixed and dried with sodium sulfate, and then the solvent was distilled away to obtain a free amine.

4.18 mmol of the ruthenium carbonyl complex shown in the above equation was placed in a 200 mL-flask, and the flask was purged with nitrogen. Then, the free amine dissolved in 33 mL of toluene was added to the flask, and the resulting mixture was heated under reflux for 60 minutes. 82 mL of Hexane was added, and then a crystal was separated by filtration under an atmosphere of nitrogen. The thus obtained crystal was washed with 10 mL of hexane and 40 mL of ethanol, and dried under a reduced pressure to obtain 1.4 g (2.3 mmol) of a ruthenium carbonyl complex 1 shown in the above equation.

[Math.1]

$^1$H-NMR (300 MHz $CD_2Cl_2$): δ=−15.23 (t, J=29.3 Hz, 1H), 2.40-2.65 (m, 4H), 2.90-3.05 (m, 2H), 3.30-3.55 (m, 2H), 3.92 (bs, 1H), 7.08-7.34 (m, 4H), 7.38-7.46 (m, 8H), 7.40-7.88 (m, 8H) $^{31}$P-NMR (121.5 MHz $CD_2Cl_2$): δ=52.8 (d, J=14 Hz)

Example 2

1-octanol was produced from N,N-dimethyloctanamide according to the following equation

[Chem. 13]

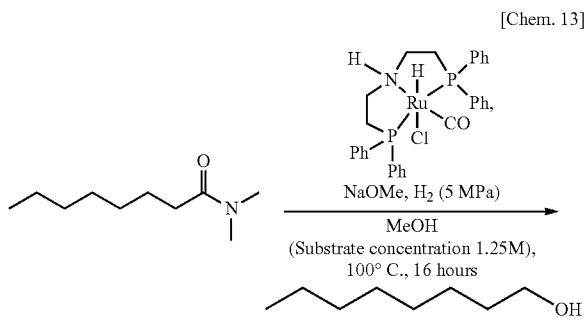

0.01 mmol of the complex 1 produced in Example 1 was placed in a 50 mL-autoclave equipped with a stirrer, and the autoclave was purged with nitrogen. 300 microliters of methanol, 1 mmol of N,N-dimethyloctanamide, and 500 microliters of methanol solution of 2.0 M sodium methoxide were added to the autoclave, and the autoclave was purged with hydrogen. The resulting mixture was stirred under hydrogen atmosphere (5 MPa) and 100 degrees C. for 16 hours to obtain a reaction solution. The reaction solution was analyzed by gas chromatography, and as a result, it was confirmed that the GC area percentage of the amide as a raw material was 2% and the GC area percentage of 1-octanol was 92%.

Examples 3 to 8

An alcohol was produced in the same manner as in Example 2 except that the type of raw material used and the amount of the catalyst were changed. The results of Examples 2 to 8 are shown in Table 1.

TABLE 1

| Sample No. | Substrate | Catalyst (mol %) | Material (GC area %) | Alcohol (GC area %) |
|---|---|---|---|---|
| 2 | H₃C(H₂C)₆C(O)N(CH₃)₂ | 1 | 2 | 92 |
| 3 | H₃C(H₂C)₆C(O)-pyrrolidine | 1 | 68 | 25 |
| 4 | H₃C(H₂C)₆C(O)NH(CH₃) | 1 | 67 | 33 |
| 5 | H₃C(H₂C)₆C(O)NH₂ | 1 | 0 | 96 |
| 6 | PhC(O)N(CH₃)₂ | 0.1 | 0 | 100 |
| 7 | PhC(O)-pyrrolidine | 1 | 9 | 89 |
| 8 | PhC(O)NH(CH₃) | 1 | 45 | 55 |

Example 9

1-octanol and aniline were produced from N-phenyloctanamide according to the following equation.

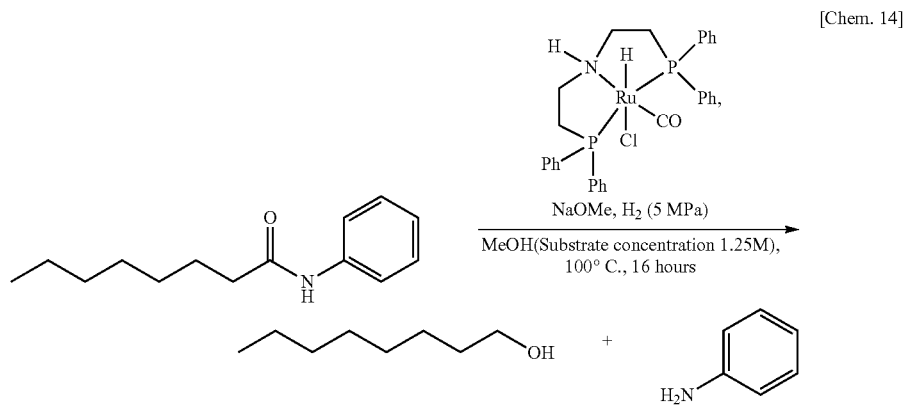

[Chem. 14]

0.01 mmol of the complex 1 produced in Example 1 and 1 mmol of N-phenyloctanamide were placed in a 50 mL-autoclave equipped with a stirrer, and the autoclave was purged with nitrogen. 300 microliters of Methanol and 500 microliters of methanol solution of 2.0 M sodium methoxide (500 microliters) were added to the autoclave, and the autoclave was purged with hydrogen. The resulting mixture was stirred under hydrogen atmosphere (5 MPa) and 100 degrees C. for 16 hours to obtain a reaction solution. The reaction solution was analyzed by gas chromatography, and as a result, it was confirmed that the amide as a raw material disappeared and the total GC area percentage of 1-octanol and aniline was 93%.

Examples 10 to 15

An alcohol and an amine were produced in the same manner as in Example 9 except that the type of raw material used and the amount of the catalyst were changed. The results of Examples 10 to 15 are shown in Table 2.

TABLE 2

| Sample No. | Substrate | Catalyst (mol %) | Material (GC area %) | Alcohol + Amine (GC area %) |
|---|---|---|---|---|
| 10 | H₃C(H₂C)₆-C(O)-NH-Ph | 1 | 0 | 93 |
| 11 | H₃C(H₂C)₆-C(O)-N(Me)-Ph | 1 | 2 | 98 |
| 12 | H₃C(H₂C)₆-C(O)-N(Ph)-Ph | 0.2 | 0 | 91 |
| 13 | Ph-C(O)-NH-Ph | 1 | 0 | 100 |

TABLE 2-continued

| Sample No. | Substrate | Catalyst (mol %) | Material (GC area %) | Alcohol + Amine (GC area %) |
|---|---|---|---|---|
| 14 | 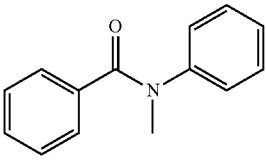 [SMILES: CN(C(=O)c1ccccc1)c1ccccc1] | 1 | 0 | 100 |
| 15 | 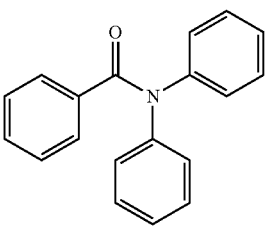 [SMILES: O=C(c1ccccc1)N(c1ccccc1)c1ccccc1] | 1 | 0 | 98 |

Example 16

Octanol and N,N-diphenylamine were produced from N,N-diphenyloctanamide according to the following equation, and were isolated by silica-gel column chromatography.

[Chem. 15]

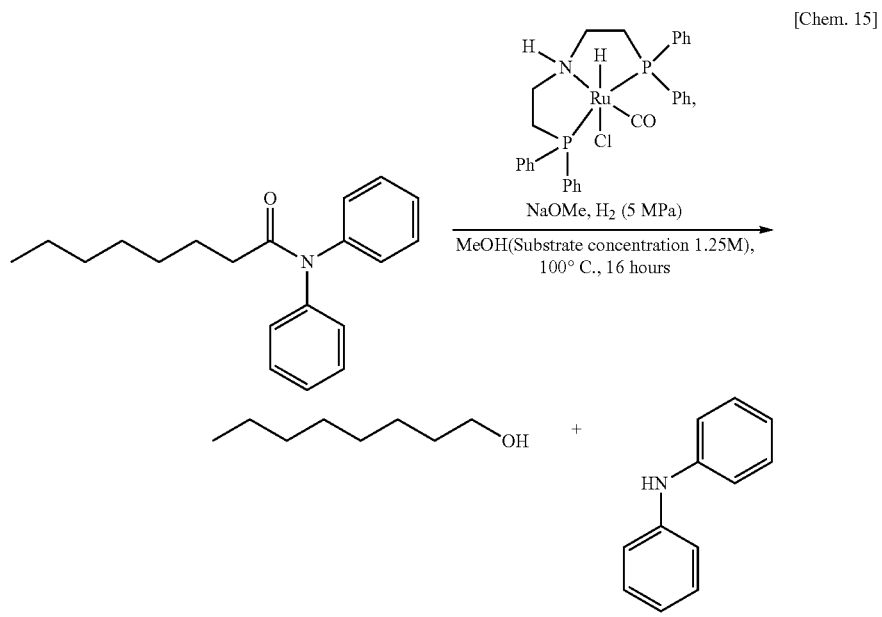

0.01 mmol of the complex 1 produced in Example 1 and 5 mmol of N,N-diphenyloctanamide were placed in a 50 mL-autoclave equipped with a stirrer, and the autoclave was purged with nitrogen. 1.5 mL of methanol and 2.5 mL of methanol solution of 2.0 M sodium methoxide were added to the autoclave, and the autoclave was purged with hydrogen. The resulting mixture was stirred under hydrogen atmosphere (5 MPa) and 100 degrees C. for 16 hours to obtain a reaction solution. After the completion of reaction, the reaction solution was cooled, diluted with 40 mL of dichloromethane, and subjected to silica gel filtration (eluting solvent: dichloromethane/methanol=10/1). The thus obtained solution was concentrated, and then the resulting residue was purified by silica gel column chromatography (silica gel: 40 g, hexane/ethyl acetate=8/1 to 4/1). As a result, 1-octanol (500 mg, 77%) and N,N-diphenylamine (800 mg, 95%) were obtained.

NMR of 1-octanol

[Math.2]

$^1$H-NMR (300 MHz CDCl$_3$): δ=3.63 (t, J=8.8 Hz, 2H), 2.00-1.46 (m, 2H), 1.40-1.30 (m, 10H), 0.90 (t, J=8.8 Hz, 3H)

NMR of N,N-diphenylamine

[Math.3]

$^1$H-NMR (300 MHz CDCl$_3$): δ=7.38-7.21 (m, 4H), 27.05-7.15 (m, 4H), 7.00-6.90 (m, 2H)

Example 17

Benzyl alcohol and N-methyl-N-phenylamine were synthesized from N-methyl-N-phenylbenzamide according to the following equation, and were isolated by silica gel column chromatography.

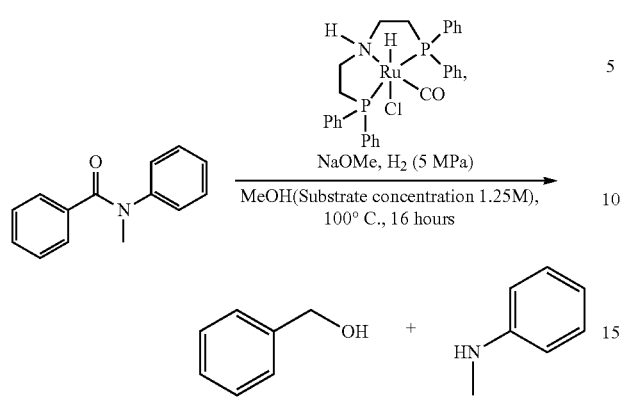

0.01 mmol of the complex 1 produced in Example 1 and 5 mmol of N-methyl-N-phenylbenzamide were placed in a 50 mL-autoclave equipped with a stirrer, and the autoclave was purged with nitrogen. 1.5 mL of Methanol and 2.5 mL of methanol solution of 2.0 M sodium methoxide were added to the autoclave, and the autoclave was purged with hydrogen. The resulting mixture was stirred under hydrogen atmosphere (5 MPa) and 100 degrees C. for 16 hours to obtain a reaction solution. After the completion of reaction, the reaction solution was cooled, diluted with 40 mL of dichloromethane, and subjected to silica gel filtration (eluting solvent: dichloromethane/methanol=10/1). The thus obtained solution was concentrated, and then the resulting residue was purified by silica gel column chromatography (silica gel: 40 g, hexane/ethyl acetate=8/1 to 4/1). As a result, benzyl alcohol (425 mg, 90%) and N-methyl-N-phenylamine (440 mg, 82%) were obtained.

NMR of benzyl alcohol
[Math.4]
$^1$H-NMR (300 MHz CDCl$_3$): δ=7.40-7.30 (m, 5H), 4.69 (s, 2H), 1.72 (brs, 1H)

NMR of N-methyl-N-phenylamine
[Math.5]
$^1$H-NMR (300 MHz CDCl$_3$): δ=7.20 (dd, J=11.6, 9.6 Hz, 2H), 6.74 (d, J=9.6 HZ, 1H), 6.65 (d, J=11.6 Hz, 2H), 3.22 (brs, 1H), 2.85 (s, 3H)

Comparative Example 1

A reaction was performed using a catalyst described in Patent Literature 2 and Non-Patent Literature 5.

0.005 mmol of Ru(acac)$_3$ and 0.01 mmol of Triphos (1,1,1-tris(diphenylphosphinomethyl)ethane) were placed in a 50 mL-autoclave equipped with a stirrer, and the autoclave was purged with nitrogen. 1.5 mL of Methanol, 5 mmol of N,N-dimethylbenzamide, and 2.5 mL of methanol solution of 2.0 M sodium methoxide were added to the autoclave, and the autoclave was purged with hydrogen. The resulting mixture was stirred under hydrogen atmosphere(5 MPa) and 100 degrees C. for 16 hours to obtain a reaction solution. The reaction solution was analyzed by gas chromatography. As a result, it was confirmed that the GC area percentage of benzyl alcohol was 1%, the GC area percentage of methyl benzoate was 12%, and the GC area percentage of N,N-dimethylbenzamide as a raw material was 86%.

The invention claimed is:
1. A method for producing an alcohol and/or an amine from an amide compound represented by the following general formula (A) under an atmosphere of hydrogen in the presence of a ruthenium carbonyl complex represented by the following general formula (1):

wherein $R^I$ represents hydrogen, an alkyl group, a cycloalkyl group, an aryl group, an aralkyl group, a heterocyclic group, an alkenyl group, an alkynyl group, or a cycloalkenyl group, these alkyl group, cycloalkyl group, aryl group, aralkyl group, heterocyclic group, alkenyl group, alkynyl group, and cycloalkenyl group may have one or more than one substituent, $R^{II}$ and $R^{III}$ may be the same or different from each other and each represents a hydrogen atom, an alkyl group, a cycloalkyl group, an aryl group, an aralkyl group, a heterocyclic group, an alkenyl group, an alkynyl group, a cycloalkenyl group, or a sulfonyl group, these alkyl group, cycloalkyl group, aryl group, aralkyl group, heterocyclic group, alkenyl group, alkynyl group, cycloalkenyl group, and sulfonyl group may have one or more than one substituent, and $R^I$ and $R^{II}$ and/or $R^{III}$ and $R^{II}$ and $R^{III}$ may be linked together to form a ring; and

wherein X and Y may be the same or different from each other and each represents an anionic ligand and L represents a tridentate aminodiphosphine ligand represented by the following general formula (2):

wherein $R^1$, $R^2$, $R^3$, and $R^4$ may be the same or different from one another and each represents a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group, $R^1$ and $R^2$ or $R^3$ and $R^4$ may be linked together to form a ring with an adjacent phosphorus atom, these alkyl group, cycloalkyl group, aryl group, aralkyl group, alkyloxy group, cycloalkyloxy group, aryloxy group, aralkyloxy group, heterocyclic group, and substituted amino group may have one or more than one substituent, $Q^1$ and $Q^2$ may be the same or different from each other and each represents a divalent alkylene group that may have one or more than one substituent, a divalent cycloalkylene group that may have one or more than one substituent, or a divalent aralkylene group that may have one or more than one substituent.

2. The production method according to claim 1, wherein the tridentate aminodiphosphine ligand L is represented by the following general formula (3):

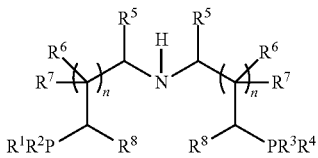

(3)

wherein $R^1$, $R^2$, $R^3$, and $R^4$ may be the same or different from one another and each represents a hydrogen atom, an alkyl group, a cycloalkyl group, an aryl group, an aralkyl group, an alkyloxy group, a cycloalkyloxy group, an aryloxy group, an aralkyloxy group, a heterocyclic group, or a substituted amino group, $R^1$ and $R^2$ or $R^3$ and $R^4$ may be linked together to form a ring with an adjacent phosphorus atom, these alkyl group, cycloalkyl group, aryl group, aralkyl group, alkyloxy group, cycloalkyloxy group, aryloxy group, aralkyloxy group, heterocyclic group, and substituted amino group may have one or more than one substituent, $R^5$, $R^6$, $R^7$, and $R^8$ may be the same or different from one another and each represents a hydrogen atom, an alkyl group that may have one or more than one substituent, a cycloalkyl group that may have one or more than one substituent, an aryl group that may have one or more than one substituent, or an aralkyl group that may have one or more than one substituent, and n is an integer of 0 to 3.

3. The production method according to claim 1, wherein the tridentate aminodiphosphine ligand L is represented by the following general formula (4):

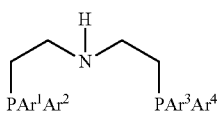

(4)

wherein $Ar^1$, $Ar^2$, $Ar^3$, and $Ar^4$ may be the same or different from one another and each represents an aryl group or an aromatic heterocyclic group, and these aryl group and aromatic heterocyclic group may have one or more than one substituent.

4. The production method according to claim 3, wherein the anionic ligand represented by X in the general formula (1) is a hydride and the anionic ligand represented by Y in the general formula (1) is Cl.

5. The production method according to claim 4, which is performed in the presence of a base.

6. The production method according to claim 5, wherein the base is sodium methoxide.

7. The production method according to claim 3, wherein $Ar^1$, $Ar^2$, $Ar^3$, and $Ar^4$ in the general formula (4) are each a phenyl group that may have one or more than one substituent.

8. The production method according to claim 7, wherein the tridentate aminodiphosphine ligand L is represented by the following general formula (5):

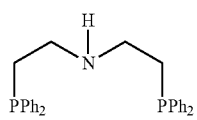

(5)

wherein Ph represents a phenyl group.

9. The production method according to claim 8, wherein the anionic ligand represented by X in the general formula (1) is a hydride and the anionic ligand represented by Y in the general formula (1) is Cl.

10. The production method according to claim 9, which is performed in the presence of a base.

11. The production method according to claim 10, wherein the base is sodium methoxide.

12. The production method according to claim 7, wherein the anionic ligand represented by X in the general formula (1) is a hydride and the anionic ligand represented by Y in the general formula (1) is Cl.

13. The production method according to claim 12, which is performed in the presence of a base.

14. The production method according to claim 13, wherein the base is sodium methoxide.

15. The production method according to claim 1, wherein the tridentate aminodiphosphine ligand L is an optically active tridentate aminodiphosphine ligand.

16. The production method according to claim 1, wherein the anionic ligand represented by X in the general formula (1) is a hydride and the anionic ligand represented by Y in the general formula (1) is Cl.

17. The production method according to claim 16, which is performed in the presence of a base.

18. The production method according to claim 17, wherein the base is sodium methoxide.

19. The production method according to claim 1, wherein the anionic ligand represented by X in the general formula (1) is a hydride and the anionic ligand represented by Y in the general formula (1) is $BH_4^-$.

* * * * *